United States Patent [19]

Shibata et al.

[11] Patent Number: 4,956,488
[45] Date of Patent: Sep. 11, 1990

[54] OPTICALLY ACTIVE CYANOBIPHENYL COMPOUND

[75] Inventors: Toshihiro Shibata; Masaki Kimura, both of Urawa, Japan

[73] Assignee: Adeka Argus Chemical Co., Ltd., Tokyo, Japan

[21] Appl. No.: 177,979

[22] Filed: Apr. 5, 1988

[30] Foreign Application Priority Data

Apr. 13, 1987 [JP] Japan .................................. 62-90150
Jun. 10, 1987 [JP] Japan ................................ 62-144948

[51] Int. Cl.$^5$ ............................................ C07C 43/02
[52] U.S. Cl. ..................................... 558/414; 558/423
[58] Field of Search ............................... 558/414, 423

[56] References Cited

U.S. PATENT DOCUMENTS 4,784,793 11/1988 Coates et al. ...................... 350/3505

OTHER PUBLICATIONS

Gray et al., Mol. Cryst. Liq. Cryst., 1976, vol 37, 189-211 (1976).
Gray et al., Chem Abstracts, vol. 86, No. 21; 155116s (1976).
Chem. Abstracts, vol. 96, No. 10; 77610p (1982).
Chem Abstracts, vol 100, No. 20; 165906w.

Primary Examiner—Mary C. Lee
Assistant Examiner—J. Richter
Attorney, Agent, or Firm—Young & Thompson

[57] ABSTRACT

The present invention discloses an optically active cyanobiphenyl compound represented by the following general formula:

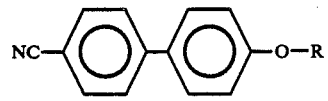

wherein, R is

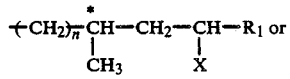

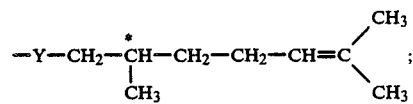

X is hydrogen atom or chlorine atom: when X is hydrogen atom, $R_1$ is normal alkyl having from 1 to 11 carbon atoms and when X is chlorine atom, $R_1$ is hydrogen atom or normal alkyl having from 1 to 11 carbon atoms; n is 3 to 5; Y is —CH$_2$— or —CO—; and * represents an asymmetric carbon atom.

15 Claims, No Drawings

OPTICALLY ACTIVE CYANOBIPHENYL COMPOUND

BACKGROUND OF THE INVENTION

1. Field of the Invention

This invention releates to a positive dielectric anisotropic cyanobiphenyl compound which is useful as a liquid crystal compound.

2. Description of the Prior Art

The positive dielectric anisotropic optically active liquid crystal is used for display element of twisted nematic type and display element of cholestericnematic phase transition type.

The liquid crystal used for above-mentioned display elements is expected to be stable chemically and optically, and expected to show stable state of liquid crystals under the condition from low to high temperature. However, a compound which gives such conditions satisfaction have apparently not been known, so that several kinds of liquid crystal compound are used as mixture.

For example, it is known that the mixtures of 4-n-alkyl or alkoxy-4'-cyanobiphenyl compound can obtain liquid crystal phase under comparative wide temperature range, however the temperature of crystal-liquid crystal phase transition of these mixtures is more than $-10°$ C., and it can not be satisfactory one.

Moreover, 4-(2-methylbutyl)-4'-cyanobiphenyl is known as a liquid crystal compound which gives cholesteric phase, however, this compound has a demerit, that is to say, the temperature of liquid crystal-isotropic liquid phase transition of this compound is too low (about $-30°$ C.), therefore a quantities of compound are needed to add in order to obtain the aimed property.

SUMMARY OF THE INVENTION

It is the object of the present invention to provide an optically active cyanobiphenyl compound useful as a liquid crystal compound.

The present invention provide a compound of following general formula.

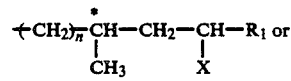

wherein, R is

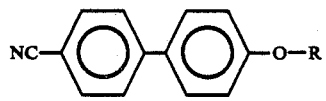

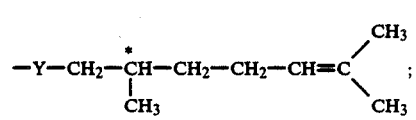

X is hydrogen atom or chlorine atom; when X is hydrogen atom, $R_1$ is normal alkyl having from 1 to 11 carbon atoms and when X is chlorine atom, $R_1$ is hydrogen atom or normal alkyl having from 1 to 11 carbon atoms; n is 3 to 5; Y is —$CH_2$— or —CO—; and * represents an asymmetric carbon atom.

DETAILED DESCRIPTION OF THE INVENTION

The compound of the present invention as represented by the above general formula can be prepared by conventional method.

For example, it may be prepared by reacting 4-hydroxy-4'-cyanobiphenyl with corresponding optically active alkyl tosylate or citronellic acid.

To further illustrate the present invention, the following Examples will be given.

EXAMPLE 1

Synthesis of 4-(6"-chloro-4"-methylhexyloxy)-4'-cyanobiphenyl

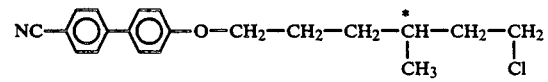

1.00 g of 4-hydroxy-4'-cyanobiphenyl, 0.43 g of pottasium hydroxide and 20 ml of methyl ethyl ketone were stirred for one hour under reflux.

6-Chloro-4-methylhexyl tosylate prepared from 1.16 g of optically active 6-chloro-4-methylhexanol ($[\alpha]_D = -3.76°$, 27° C., C=2, chloroform solution) was added and stirred for 12 hours under reflux.

The solvent was evaporated and diethylether was added and then newtralized with 5% aqueous hydrochloric acid solution. After washed with water, the solvent was evaporated.

The product was purified on a silica gel column with the use of hexane/ether (85/15) as a developing solvent. Thus 1.3 g of 4-(6"-chloro-4"-methylhexyloxy)-4'-cyanobiphenyl was obtained.

Infrared spectroscopy (cm$^{-1}$). 3050(w), 2950(s), 2860(m), 2220(s), 1600(vs), 1490(s), 1465(m), 1245(vs), 1035(w), 820(s) and 655(w).

Optical rotation. $[\alpha]_D = +3.79°$ (C=1, CHCl$_3$ solution, 27° C.)

This compound was poured into a transparent glass electrode cell of 2 μm in thickness, which had been subjected to orientation by rubbing, and heated to 90° C. to thereby give an isotropic liquid.

The following phase transition was observed under a polarization microscope.

$$\text{Iso} \xrightarrow[20]{} \text{Ch} \xrightleftharpoons[<-15]{} \text{Cry} \; (°C.)$$

Iso: isotropic, Ch: cholesteric
Cry: crystal

EXAMPLE 2

Synthesis of 4-(6''-chloro-4''-methyloctoxy)-4'-cyanobiphenyl

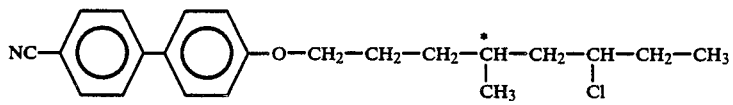

The procedure of Example 1 was followed except that the 6-chloro-4-methylhexyl tosylate was replaced by 6-chloro-4-methyloctyl tosylate prepared from optically active 6-chloro-4-methyloctanol ($[α]_D = +0.75°$, 28° C., C=1, chloroform solution) to thereby give the title compound.

Infrared spectroscopy ($cm^{-1}$). 3050(w), 2975(s), 2890(m), 2240(s), 1605(vs), 1500(vs), 1470(m), 1255(vs), 1040(w), 825(s) and 665(w)

Optical rotation. $[α]_D = +7.87°$ (C=1, CHCl$_3$ solution, 27° C.)

Phase transition.

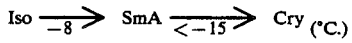

SmA: smectic

EXAMPLE 3

Synthesis of 4-(4''-methyloctoxy)-4'-cyanobiphenyl

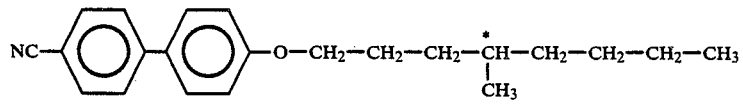

The procedure of Example 1 was followed except that the 6-chloro-4-methylhexyl tosylate was replaced by 4-methyloctyl tosylate prepared from optically active 4-methyloctanol ($[α]_D = -1.41°$, 27° C., C=2, chloroform solution) to thereby give the title compound.

Infrared spectroscopy ($cm^{-1}$). 3050(w), 2940(s), 2860(m), 2230(m), 1605(s), 1495(s), 1460(m), 1250(s), 1035(w) and 825(vs)

Phase transition.

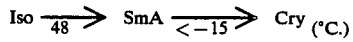

EXAMPLE 4

Synthesis of 4-(6''-methyldecyloxy)-4'-cyanobiphenyl

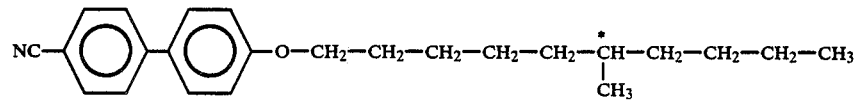

The procedure of Example 1 was followed except that the 6-chloro-4-methylhexyl tosylate was replaced by 6-methyldecyl tosylate prepared from optically active 6-methyldecanol ($[α]_D = -0.62°$, 27° C., C=2, chloroform solution) to thereby give the title compound.

Infrared spectroscopy ($cm^{-1}$). 3050(w), 2940(s), 2860(m), 2230(m), 1605(s), 1495(s), 1460(m), 1250(s), 1035(w) and 825(vs)

Phase transition.

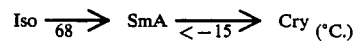

EXAMPLE 5

Synthesis of (R)-4-citronelloyloxy-4'-cyanobiphenyl

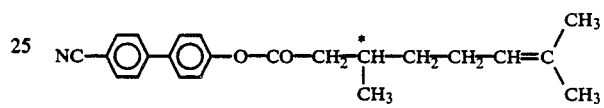

0.84 g of (R)-citronellic acid and 0.96 g of 4-hydroxy-4'-cyanobiphenyl, 10 ml of dichloroethane 1.13 g of N,N'-dicyclohexyl carbodiimide and 0.1 g of 4-pyrolidinopyridine were stirred for 3 hours at room temperature.

The solvent was evaporated and ethyl acetate was added therein, and precipitated N,N'-dicyclohexyl urea were filtered and the filtrate was evaporated.

The product was purified on a silica gel column with the use of hexane/ether (8/2) as a developing solvent. Thus(R)-4-citronelloyloxy-4'-cyanobiphenyl was obtained.

Infrared spectroscopy ($cm^{-1}$). 2950(s), 2230(m), 1750(s), 1600(m), 1180(s), 1120(s) and 830(s).

Optical rotation. $[α]_D = +6.26°$ (C=1, CHCl$_3$ solution, 25° C.).

Phase transition.

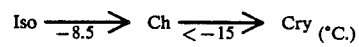

EXAMPLE 6

Synthesis of (R)-4-citronellyloxy-4'-cyanobiphenyl

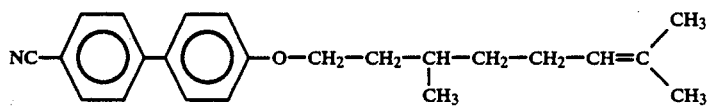

1.00 g of 4-hydroxy-4'-cyanobiphenyl, 0.24 g of pottasium hydroxide and 10 ml of dioxane were stirred for one hour under reflux.

1.6 g of (R)-citronellyl tosylate was added and stirred for 10 hours under reflux.

The solvent was evaporated and diethylether was added and then newtralized with 5% aqueous hydrochloric acid solution. After washed with water, the solvent was evaporated.

The product was purified on a silica gel column with the use of hexane/ether (9/1) as a developing solvent. Thus 1.4 g of (R)-4-citronellyloxy-4'-cyanobiphenyl was obtained.

Infrared spectroscopy (cm$^{-1}$). 3050(w), 2950(s), 2230(s), 1600(s), 1495(s), 1290(m), 1250(s), 1180(m) and 820(s).

Optical rotation. $[\alpha]_D = +3.86°$ (C=1, CHCl$_3$ solution, 25° C.).

Phase transition.

$$\text{Iso} \xrightarrow{10.5} \text{SmA} \xrightarrow{<-15} \text{Cry} \text{ (°C.)}$$

What is claimed is:

1. An optically active cyanobiphenyl compound represented by the following general formula:

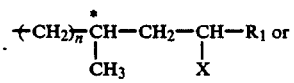

wherein, R is

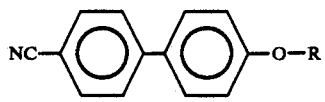

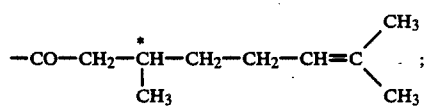

X is hydrogen atom or chlorine atom; when X is hydrogen atom, R$_1$ is straight chain alkyl having from 1 to 11 carbon atoms and when X is chlorine atom, R$_1$ is hydrogen atom or straight chain alkyl having from 1 to 11 carbon atoms; n is 3 to 5; and * represents an asymmetric carbon atom.

2. A cyanobiphenyl compound as claimed in claim 1 in which R is

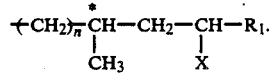

3. A cyanobiphenyl compound as claimed in claim 2 in which X is chlorine atom.

4. A cyanobiphenyl compound as claimed in claim 2 in which X is hydrogen atom.

5. A cyanobiphenyl compound as claimed in claim 2 in which X is chlorine atom and R$_1$ is hydrogen atom.

6. A cyanobiphenyl compound as claimed in claim 2, in which R$_1$ is straight-chain alkyl having from 1 to 11 carbon atoms.

7. A cyanobiphenyl compound as claimed in claim 2, in which n is 3.

8. A cyanobiphenyl compound as claimed in claim 2, in which n is 5.

9. A cyanobiphenyl compound of claim 1 designated 4-(6''-chloro-4''-methylhexyloxy)-4'-cyanobiphenyl.

10. A cyanobiphenyl compound of claim 1 designated 4-(6''-chloro-4''-methyloctoxy)-4'-cyanobiphenyl.

11. A cyanobiphenyl compound of claim 1 designated 4-(4''-methyloctoxy)-4'-cyanobiphenyl.

12. A cyanobiphenyl compound of claim 1 designated 4-(6''-methyldecyloxy)-4'-cyanobiphenyl.

13. A cyanobiphenyl compound of claim 1 designated (R)-4-citronelloyloxy-4'-cyanobiphenyl.

14. A cyanobiphenyl compound of claim 1 designated (R)-4-citronellyloxy-4'-cyanobiphenyl.

15. An optically active cyanobiphenyl compound represented by the following general formula:

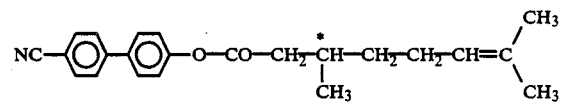

wherein * represents an asymmetric carbon atom.

* * * * *